US012678636B2

(12) United States Patent <br> Connolly et al.

(10) Patent No.: US 12,678,636 B2 <br> (45) Date of Patent: Jul. 14, 2026

(54) APPARATUS FOR OPTICAL SURFACE MONITORING CALIBRATION AND RESPIRATORY CYCLE SIMULATION

(71) Applicant: SIEMENS HEALTHINEERS INTERNATIONAL AG, Steinhausen (CH)

(72) Inventors: Ruth Connolly, Princeton, NJ (US); Candice Brunscheen, Las Vegas, NV (US); Stephen Mohr, Danville, CA (US); Edwin Von Borstel, East Palo Alto, CA (US); Daisha Puccinelli, Henderson, NV (US)

(73) Assignee: SIEMENS HEALTHINEERS INTERNATIONAL AG (CH)

( * ) Notice: Subject to any disclaimer, the term of this patent is extended or adjusted under 35 U.S.C. 154(b) by 189 days.

(21) Appl. No.: 18/522,157

(22) Filed: Nov. 28, 2023

(65) Prior Publication Data

US 2025/0170423 A1 May 29, 2025

(51) Int. Cl.
*A61N 5/10* (2006.01)

(52) U.S. Cl.
CPC ......... *A61N 5/1049* (2013.01); *A61N 5/1037* (2013.01); *A61N 5/1069* (2013.01); *A61N 5/1075* (2013.01); *A61N 2005/1059* (2013.01); *A61N 2005/1076* (2013.01)

(58) Field of Classification Search
CPC .. A61N 5/1037; A61N 5/1049; A61N 5/1069; A61N 5/1075; A61N 2005/1059; A61N 2005/1076
See application file for complete search history.

(56) References Cited

U.S. PATENT DOCUMENTS

| | | | | | |
|---|---|---|---|---|---|
| 12,023,522 | B2 * | 7/2024 | Kerns | .................. | A61N 5/1075 |
| 2006/0002519 | A1 * | 1/2006 | Jenkins | ................ | A61N 5/1048 |
| | | | | | 378/207 |
| 2008/0240364 | A1 * | 10/2008 | Main | ..................... | A61N 5/1048 |
| | | | | | 250/252.1 |
| 2012/0080578 | A1 * | 4/2012 | Thieme-Marti | ...... | A61N 5/1049 |
| | | | | | 248/371 |
| 2019/0175951 | A1 * | 6/2019 | Yu | .......................... | A61B 6/032 |
| 2023/0084185 | A1 * | 3/2023 | Magaz | ................. | A61N 5/1075 |
| | | | | | 702/116 |
| 2023/0190221 | A1 * | 6/2023 | Stamm | ................... | A61B 5/055 |
| | | | | | 378/207 |
| 2023/0330437 | A1 * | 10/2023 | Kerns | .................. | A61N 5/1075 |

* cited by examiner

*Primary Examiner* — Mark R Gaworecki

(74) *Attorney, Agent, or Firm* — SU IP CONSULTING

(57) ABSTRACT

An apparatus for a treatment delivery system includes a base with a first surface for resting on a patient-receiving surface of a couch of the treatment delivery system and a second surface; and a movable surface that is included in the second surface and can be actuated in a first direction away from the couch and in a second direction toward the couch. Alternatively or additionally an apparatus for a treatment delivery system includes a base with a first surface for resting on a patient-receiving surface of a couch of the treatment delivery system and a second surface; and a movable surface that is included in the second surface and can be actuated in a first direction away from the couch and in a second direction toward the couch.

14 Claims, 8 Drawing Sheets

APPARATUS FOR OPTICAL SURFACE MONITORING CALIBRATION AND RESPIRATORY CYCLE SIMULATION

BACKGROUND

Unless otherwise indicated herein, the approaches described in this section are not prior art to the claims in this application and are not admitted to be prior art by inclusion in this section.

Radiation therapy is a localized treatment for a specific target tissue (a planning target volume), such as a cancerous tumor. Ideally, radiation therapy is performed on a planning target volume that spares the surrounding normal tissue from receiving doses above specified tolerances, thereby minimizing risk of damage to healthy tissue. Prior to radiation therapy, an imaging system is typically employed to provide a three-dimensional image of the target tissue and surrounding area, referred to as the "treatment planning image." From such imaging, the size and mass of the target tissue can be estimated, a planning target volume determined, and an appropriate treatment plan generated.

So that the prescribed dose is correctly supplied to the planning target volume (i.e., the target tissue) during radiation therapy, before a radiation treatment session (or fraction), the patient is correctly positioned relative to the linear accelerator that provides the radiation therapy. Typically, an imaging system is used to view target tissues immediately before delivery of the radiation therapy so that the target tissues can be viewed using a reconstructed region of patient anatomy based on X-ray images of the target tissues. Further, in the case of surface guided radiation therapy (SGRT), stereo vision technology precisely monitors a patient's surface during patient setup and treatment. This monitoring facilitates the alignment of a patient's body with a planned patient body outline and tracks patient motion throughout treatment.

SUMMARY

According to various embodiments, an apparatus for a radiation therapy system enables the positioning of an optical calibration plate accurately, efficiently, and reproducibly for correct calibration of one or more projector cameras of a surface guidance system associated with the radiation therapy system. In the embodiments, the optical calibration plate can be accurately located at a specified longitudinal position on a treatment couch of a radiation therapy system and accurately oriented at a specified calibration angle. The optical calibration plate can be maintained at the specified calibration angle even when repositioned laterally on the treatment couch as part of the calibration process. Additionally, or alternatively, according to various embodiments, an apparatus for a radiation therapy system enables the demonstration of various use cases of the surface guidance system (including radiation treatment with respiratory gating, auto-beam hold, and patient motion monitoring). In the embodiments, the apparatus includes a movable anthropomorphic surface that can simulate chest wall motion during a patient respiratory cycle. As a result, the demonstration of and user training for such use cases can be performed without relying on a patient, trainer, or other proxy lying on the couch.

In some embodiments, an apparatus for a treatment delivery system includes: a base with a first surface for resting on a patient-receiving surface of a couch of the treatment delivery system and a second surface; and a movable surface that is included in the second surface and can be actuated in a first direction away from the couch and in a second direction toward the couch. Alternatively or additionally an apparatus for a treatment delivery system includes: a base for resting on a couch of the treatment delivery system; a support structure for positioning a surface of an optical calibration device at a calibration angle; and a first indexing feature that is formed on a bottom surface of the base and is configured to fix the base at a calibration position along a longitudinal axis of the couch by mating with a second indexing feature.

The foregoing summary is illustrative only and is not intended to be in any way limiting. In addition to the illustrative aspects, embodiments, and features described above, further aspects, embodiments, and features will become apparent by reference to the drawings and the following detailed description.

BRIEF DESCRIPTION OF THE DRAWINGS

The foregoing and other features of the present disclosure will become more fully apparent from the following description and appended claims, taken in conjunction with the accompanying drawings. These drawings depict only several embodiments in accordance with the disclosure and are, therefore, not to be considered limiting of its scope. The disclosure will be described with additional specificity and detail through use of the accompanying drawings.

DETAILED DESCRIPTION

Figure 1:
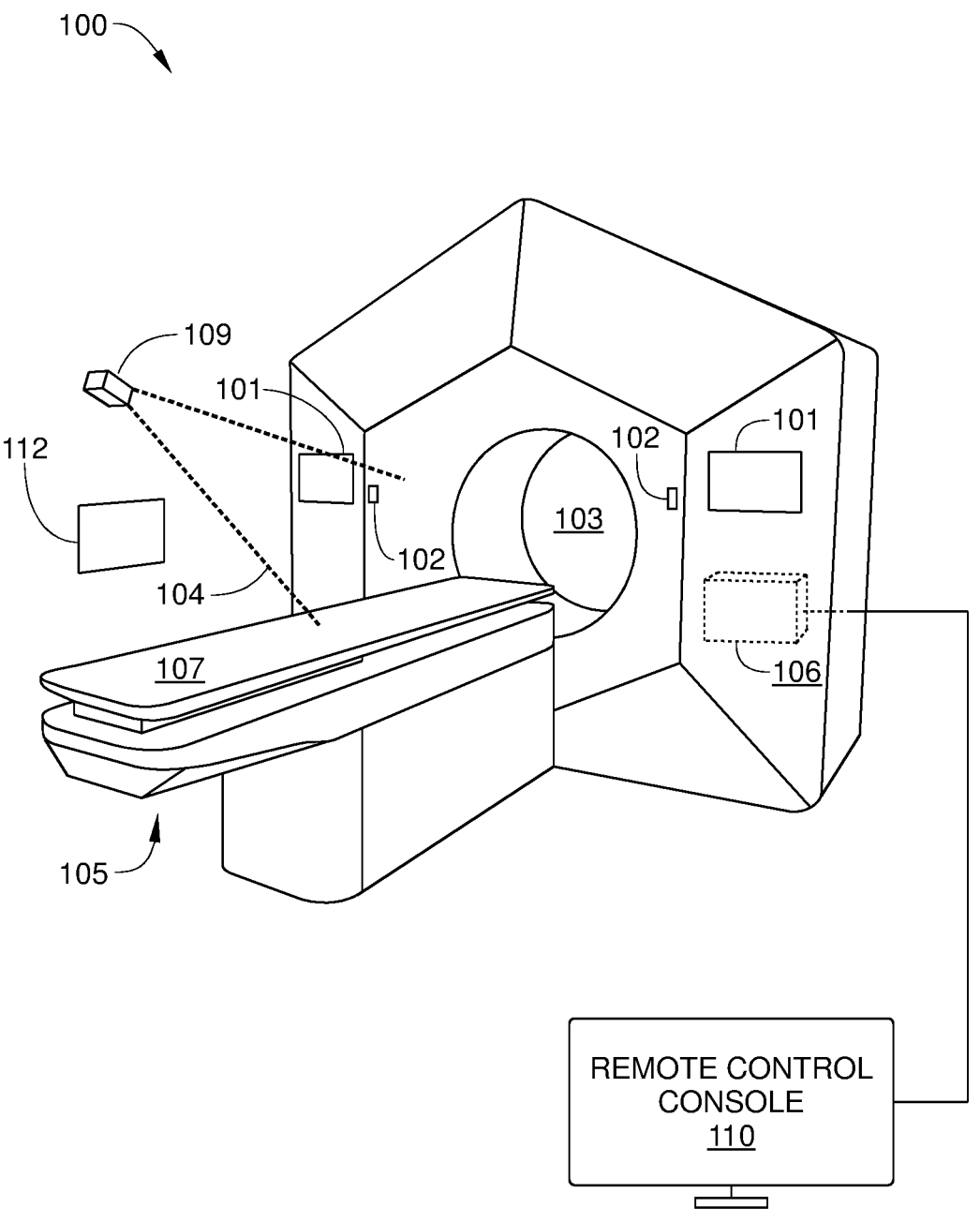
FIG. 1 is a perspective view of a treatment delivery system, according to various embodiments.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the disclosure, as generally described herein, and illustrated in the figures, can be arranged, substituted, combined, and designed in a wide variety of different configurations, all of which are explicitly contemplated and make part of this disclosure.

Introduction

Surface guided radiation therapy (SGRT) is a rapidly growing technology used to improve the accuracy of dose delivery in radiation treatment. In SGRT, optical monitoring of a patient's surface is employed during patient setup and treatment to precisely track patient motion and position in three-dimensions. Such optical monitoring provides feedback to the radiation therapist or other user indicating precisely how the current patient surface position differs from a planned patient position, which is the ideal patient position for accurate dosing during a particular treatment session or fraction. Therefore, the use of real-time optical monitoring of a patient surface facilitates patient setup, interfraction positioning, and intrafraction patient motion detection. As noted previously, there are issues associated with the calibration of surface guidance systems as well as performing training for certain surface guidance system use cases.

For a surface guidance system to be capable of providing accurate real-time patient surface monitoring, the system must be calibrated with respect to the associated radiation therapy system. Typically, to prevent a false offset from being reported by the surface guidance system, this calibration includes alignment of the isocenter of the surface guidance system to an isocenter of the radiation therapy system, such as the rotation axis of the treatment couch. Otherwise, these two isocenters may not be coincident and, when the treatment couch is rotated to a non-zero table angle, a reference patient surface employed by the surface guidance system will be misaligned with respect to the actual patient position in the lateral and longitudinal axes of the treatment couch.

Generally, isocenter calibration of a surface guidance system relies on the precise and repeatable placement of an optical calibration plate at a specific calibration angle relative to the camera or cameras included in the surface guidance system. In some instances, isocenter calibration involves repositioning the optical calibration plate to multiple locations on the treatment couch while precisely maintaining the calibration angle. For example, the optical calibration plate may be translated laterally on the treatment couch to different positions. However, even small deviations in the orientation of the optical calibration plate from the required calibration angle can result in misalignment between the isocenter of the surface guidance system and the isocenter of the radiation therapy system. As a result, isocenter calibration of a surface guidance system can be time-consuming and prone to error. Further, when inconsistent positioning of the optical calibration plate causes marginal misalignment between the isocenter of the surface guidance system and the isocenter of the radiation therapy system, such misalignment may not be detected until subsequent testing of the surface guidance system is completed. In such instances, the isocenter calibration must be performed again, causing significant delay in the commissioning of the surface guidance system Oftentimes, a surface guidance system can support various beneficial functionalities, including radiation treatment with respiratory gating and/or patient motion monitoring. In addition, a radiation therapy system may have an auto-beam hold functionality, in which X-ray imaging monitors implanted fiducials in the patient during radiation treatment. However, each of these functionalities requires specifically tailored training for clinical end-users. Because conventional phantom systems only demonstrate internal motion, such training typically involves a trainer who is conducting demonstrations and training to also simulate the presence of a patient by lying on the treatment couch. Of course, this can be cumbersome or impractical, for example when the presence of a trainer is also required at the user interface of the surface guidance system. Alternately, such training can be performed with patient involvement, but this results in longer on-couch time for the patients, which can be uncomfortable for the patient and is highly undesirable.

In light of the above, there is a need in the art for improved techniques for performing calibration of and training for surface guidance systems employed in conjunction with radiation therapy.

System Overview

FIG. 1 is a perspective view of a treatment delivery system 100 that can beneficially implement various embodiments. Treatment delivery system 100 delivers a treatment fraction to a region of patient anatomy as indicated by a treatment plan for the patient. Thus, treatment delivery system 100 is configured to perform radiotherapy in conjunction with optical monitoring of a patient surface, and therefore is capable of performing surface guided radiation therapy (SGRT) and/or provide real-time feedback for patient and accessory setup prior to delivery of a treatment fraction.

In some embodiments, treatment delivery system 100 includes an imaging system configured to image patient anatomy using X-ray imaging techniques. For example, in some embodiments, treatment delivery system 100 is configured to provide stereotactic radiosurgery and precision radiotherapy for lesions, tumors, and conditions anywhere in the body where radiation treatment is indicated. As such, treatment delivery system 100 can include one or more of a linear accelerator (LINAC) that generates a megavolt (MV) treatment beam of high energy X-rays, one or more kilovolt (kV) X-ray sources, one or more X-ray imagers, and, in some embodiments, an MV electronic portal imaging device (EPID). By way of example, treatment delivery system 100 is described herein configured with a circular gantry. In other embodiments, treatment delivery system 100 can be configured with a C-gantry capable of infinite rotation via a slip ring connection. In yet other embodiments, treatment delivery system 100 can be configured with an imaging system having an MRI-based imaging capability.

In some embodiments, treatment delivery system 100 is capable of kV imaging of a target volume immediately prior to or during application of an MV treatment beam, so that an IGRT and/or an intensity-modulated radiation therapy (IMRT) process can be performed using X-ray imaging. In some instances, such kV imaging can include planar kV imaging. Alternatively or additionally, in some instances, such kV imaging can include cone-beam computed tomography (CBCT) imaging.

Treatment delivery system 100 may include one or more touchscreens 101, couch motion controls 102, a bore 103, a base positioning assembly 105, a couch 107 disposed on base positioning assembly 105, and an image acquisition and treatment control computer 106, all of which are disposed within a treatment room. Treatment delivery system 100 further includes a remote control console 110, which is disposed outside the treatment room and enables treatment delivery and patient monitoring from a remote location. Base positioning assembly 105 is configured to precisely position couch 107 with respect to bore 103, and motion controls 102 include input devices, such as button and/or switches, that enable a user to operate base positioning assembly 105 to automatically and precisely position couch 107 to a predetermined location with respect to bore 103. Motion controls 102 also enable a user to manually position couch 107 to a predetermined location.

In some embodiments, treatment delivery system 100 is associated with or includes a surface guidance system that provides real-time optical monitoring of a patient surface for patient setup and/or interfraction positioning. Additionally or alternatively, in some embodiments, the surface guidance system provides real-time optical monitoring of a patient surface for detection of intrafraction patient motion. In some embodiments, the surface guidance system can generate a surface map of the surface of a patient positioned on couch 107 and within a field of view 104. In some embodiments, the surface guidance system includes one or more patient-monitoring sensors 109 and an output device 112, such as a display screen located proximate couch 107. In the embodiment illustrated in FIG. 1, output device 112 is depicted as a wall-mounted display screen proximate couch 107. Alternatively or additionally, in some embodiments, output device 112 is disposed outside the treatment room, for example proximate remote control console 110. In operation, the surface map and/or indicators showing offsets between a current patient position and a planned patient position are displayed on output device 112. In some embodiments, patient-monitoring sensors 109 can include stereo vision cameras, time-of-flight sensors, surface scanners, and/or the like for computing a live 3D mesh of a surface of a patient positioned on couch 107. Thus, the surface guidance system that includes patient-monitoring sensors 109 can be used for the setup of a patient and/or patient positioning accessories, interfraction positioning, and intrafraction patient motion detection.

Examples of use cases of treatment delivery system 100 that employ the surface guidance system can include radiation treatment with respiratory gating and patient motion monitoring. In respiratory gating use cases, radiation is only delivered when a tumor or target volume is disposed within a predefined "window" that is based on motion of the surface of the patient. Thus, radiation is being delivered to the tumor or target volume when the tumor or target volume is correctly located. For example, in some instances, some gating systems will automatically turn off a treatment beam when the tumor or target volume leaves the predefined window and then turn on the treatment beam when the tumor or target volume again enters the predefined window. Alternatively, in some instances, a treatment beam is turned off manually by an operator when the tumor or target volume leaves the predefined window and then turned on by the operator when the tumor or target volume again enters the predefined window. In patient motion monitoring use cases, when a position offset of a patient on couch 107 exceeds a predefined offset threshold during treatment, such displacement is detected via the surface guidance system. In response, a treatment beam can be automatically turned off and the patient can be repositioned for further treatment.

In some embodiments, the surface guidance system that includes patient-monitoring sensors 109 is incorporated in treatment delivery system 100. In other embodiments, the surface image guidance system can be a system external to but communicatively coupled to treatment delivery system 100, such as a stand-alone surface guidance system. In the embodiment illustrated in FIG. 1, the surface image guidance system includes a single patient-monitoring sensor 109, while in other embodiments, the surface image guidance system can include multiple patient-monitoring sensors 109. In an embodiment, the stand-alone surface guidance system may be an Identify™ surface-guided radiosurgery system commercially available from Varian, Inc., Palo Alto, Calif. and includes up to three high-precision stereovision cameras with submillimeter accuracy that have a refresh rate of 5-10 frames/second for tracking a surface of a patient in real time during treatment delivery. An embodiment of a patient-monitoring sensors 109 is described below in conjunction with FIG. 2.

Figure 2:
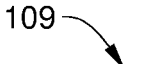
FIG. 2 schematically illustrates a patient-monitoring sensor of the treatment delivery system of FIG. 1, according to various embodiments.
Figure 2:
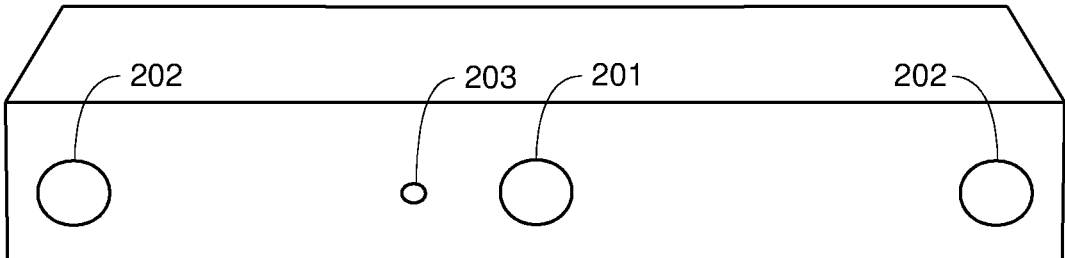

FIG. 2 schematically illustrates a patient-monitoring sensor 109 of the radiation therapy system of FIG. 1, according to various embodiments. In the embodiment illustrated in FIG. 2, patient-monitoring sensor 141 includes a projector 201, two image sensors 202 or cameras, and a calibration light-emitting diode (LED) 203. In operation, projector 201 projects a pseudo-random speckle pattern onto the surface of a patient, for example disposed on couch 107 (shown in FIG. 1). The random speckle pattern provides texture variations employed in the surface reconstruction process. Image sensors 202 then acquire the raw textured data used for the 3D surface reconstruction. A controller of a surface guidance system then performs a 3D surface reconstruction process. In the 3D surface reconstruction process, projected and captured patterns are compared to identify the coordinates of each pixel in the captured image.

Figure 3:
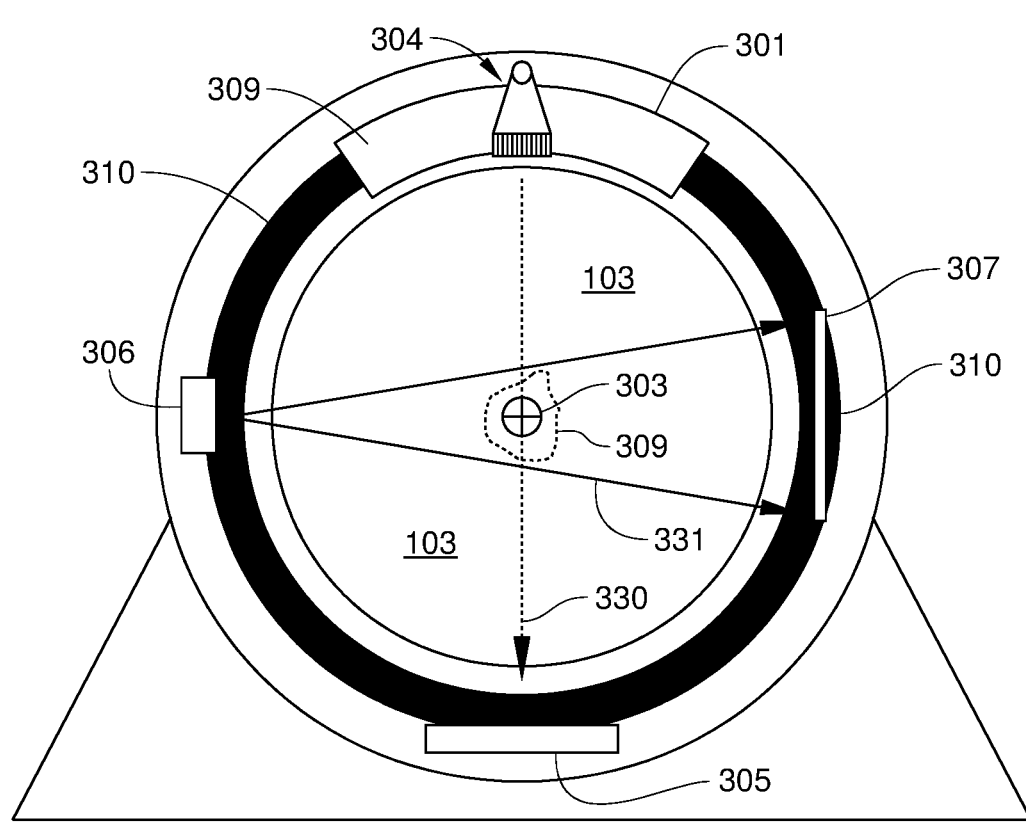
FIG. 3 schematically illustrates a drive stand and gantry of the treatment delivery system of FIG. 1, according to various embodiments.

FIG. 3 schematically illustrates a drive stand 300 and gantry 310 of treatment delivery system 100, according to various embodiments. Covers, base positioning assembly 105, couch 107, and other components of treatment delivery system 100 are omitted in FIG. 3 for clarity. Drive stand 300 is a fixed support structure for components of treatment delivery system 100, including gantry 310 and a drive system 301 for rotatably moving gantry 310. Drive stand 300 rests on and/or is fixed to a support surface that is external to treatment delivery system 100, such as a floor of a radiotherapy treatment facility. Gantry 310 is rotationally coupled to drive stand 300 and is a support structure on which various components of treatment delivery system 100 are mounted, including a linear accelerator (LINAC) 304, an MV electronic portal imaging device (EPID) 305, an imaging X-ray source 306, and an X-ray imager 307. During operation of treatment delivery system 100, gantry 320 rotates about bore 103 when actuated by drive system 301.

Drive system 301 rotationally actuates gantry 310. In some embodiments, drive system 301 includes a linear motor that can be fixed to drive stand 300 and interacts with a magnetic track (not shown) mounted on gantry 310. In other embodiments, drive system 301 includes another suitable drive mechanism for precisely rotating gantry 310 about bore 301. LINAC 304 generates an MV treatment beam 330 of high energy X-rays (or in some embodiments electrons, protons, and/or other heavy charged particles, ultra-high dose rate X-rays (e.g., for FLASH radiotherapy) or microbeams for microbeam radiation therapy) and EPID 305 is configured to acquire X-ray images with treatment beam 330. Imaging X-ray source 306 is configured to direct a conical beam of X-rays, referred to herein as imaging X-rays 331, through an isocenter 303 of treatment delivery system 100 to X-ray imager 307, and isocenter 303 typically corresponds to the location of a target volume 309 to be treated. In the embodiment illustrated in FIG. 3, X-ray imager 307 is depicted as a planar device, whereas in other embodiments, X-ray imager 307 can have a curved configuration.

X-ray imager 307 receives imaging X-rays 331 and generates suitable projection images therefrom. According to certain embodiments, such projection images can then be employed to construct or update portions of imaging data for a digital volume that corresponds to a three-dimensional (3D) region that includes target volume 309. That is, a 3D image of such a 3D region is reconstructed from the projection images. In some embodiments, CBCT and/or digital tomosynthesis (DTS) can be used to process the projection images generated by X-ray imager 307. CBCT is often employed at the beginning of and/or during a radiation therapy session to generate a set-up 3D reconstruction. For example, CBCT may be employed immediately prior to application of treatment beam 330 to generate a 3D reconstruction confirming that target volume 309 has not moved or changed shape. In such embodiments, the 3D reconstruction can be employed in a beam-hold operation, in which the detected positions of implanted fiducial markers are compared to planned positions of such markers. When there is a sufficient discrepancy between the detected positions and the planned positions, treatment beam 330 is paused.

In the embodiment illustrated in FIG. 3, treatment delivery system 100 includes a single X-ray imager and a single corresponding imaging X-ray source. In other embodiments, treatment delivery system 100 can include two or more X-ray imagers, each with a corresponding imaging X-ray source.

The projection images generated by X-ray imager 307 in FIG. 3 are used prior to and/or during treatment to reconstruct a 3D digital volume of an object or portion of patient anatomy, such as a 3D region of patient anatomy that includes target volume 309. In some instances, such X-ray projection images, or a reconstructed 3D digital volume, are employed for initial patient positioning on couch 107. Such a reconstructed 3D digital volume includes a plurality of voxels of anatomical image data, where each voxel corresponds to a different location within the digital volume. Generally, the digital volume corresponds to a 3D region that includes a target volume.

For purposes of discussion, the target volume can refer to the gross tumor volume (GTV), clinical target volume (CTV), or the planning target volume (PTV) for a particular treatment. The GTV depicts the position and extent of the gross tumor, for example what can be seen or imaged; the CTV includes the GTV and an additional margin for subclinical disease spread, which is generally not imageable; and the PTV is a geometric concept designed to ensure that a suitable radiotherapy dose is actually delivered to the CTV without adversely affecting nearby organs at risk. Thus, the PTV is generally larger than the CTV, but in some situations can also be reduced in some portions to provide a safety margin around an organ at risk. The PTV is typically determined based on imaging performed prior to the time of treatment, and alignment of the PTV with the current position of patient anatomy at the time of treatment is facilitated by X-ray imaging of a digital volume.

In the embodiment of treatment delivery system 100 described above, radiation therapy system 100 is described herein configured with a circular gantry and a bore into which a treatment couch is translated to position a patient for treatment. In other embodiments, treatment delivery system 100 can be configured with a C-gantry capable of infinite rotation via a slip ring connection. In such embodiments, a couch positioning assembly of treatment delivery system 100 may be configured to rotate the treatment couch about an isocenter if the treatment delivery system to one or more treatment positions. One such embodiment is described below in conjunction with FIG. 4.

Figure 4:
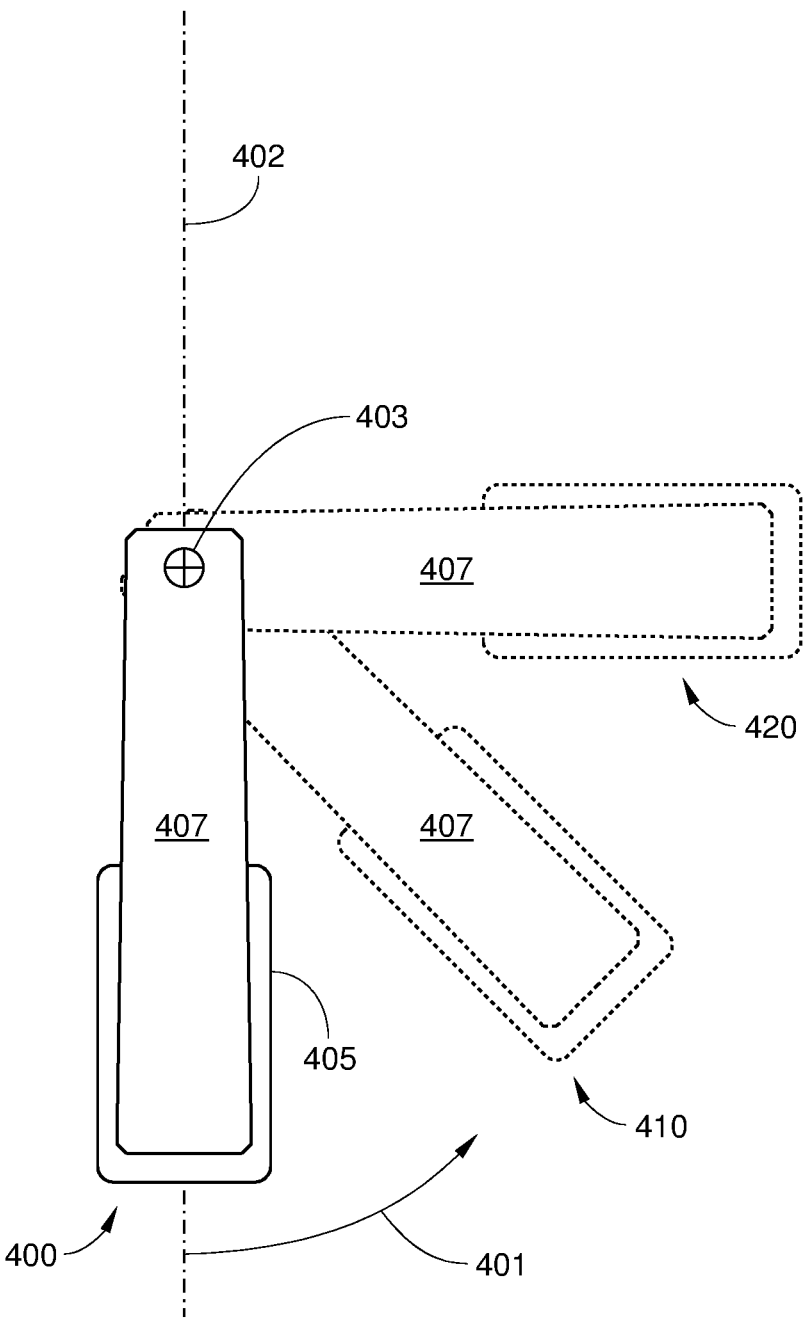
FIG. 4 schematically illustrates plan views of a treatment couch 407 in various treatment positions, according to various embodiments.

FIG. 4 schematically illustrates plan views of a treatment couch 407 in various treatment positions, according to various embodiments. FIG. 4 includes a plan view of treatment couch 407 in a neutral position 400, in which treatment couch 407 is in line with a horizontal rotation axis 402 of a C-arm gantry (not shown for clarity). Also shown in the plan view of FIG. 4 is a first rotated position 410 (dashed lines), in which treatment couch 407 is rotated 45 degrees from neutral position 400, and a second rotated position 420 (dashed lines), in which treatment couch 407 is rotated 90 degrees from neutral position 400. As shown, a couch positioning assembly 405 rotates treatment couch 407 about an isocenter 403 to a specified couch rotational angle 401 from neutral position 400. Couch rotational angle 401 can be, for example, up to about 90 degrees.

In the embodiment illustrated in FIG. 4, isocenter 403 corresponds to a mechanical isocenter of treatment couch 407 and couch positioning assembly 405, such as a point around which treatment couch 407 and couch positioning assembly 405 are rotated during operation. Alternatively or additionally, in some embodiments, isocenter 403 corresponds to an imaging and/or treatment isocenter of the treatment delivery system that includes treatment couch 407, such as isocenter 303 in FIG. 3. It is noted that for a surface guidance system to accurately perform 3D surface reconstructions, an isocenter of the surface guidance system is aligned with an isocenter of the associated treatment delivery system, such as isocenter 303 or isocenter 403, via a calibration process. According to various embodiments, a calibration and training apparatus facilitates such a calibration process. Embodiments of the calibration and training apparatus are described below in conjunction with FIGS. 5A and 5B.

Calibration and Training Apparatus

Figure 5A:
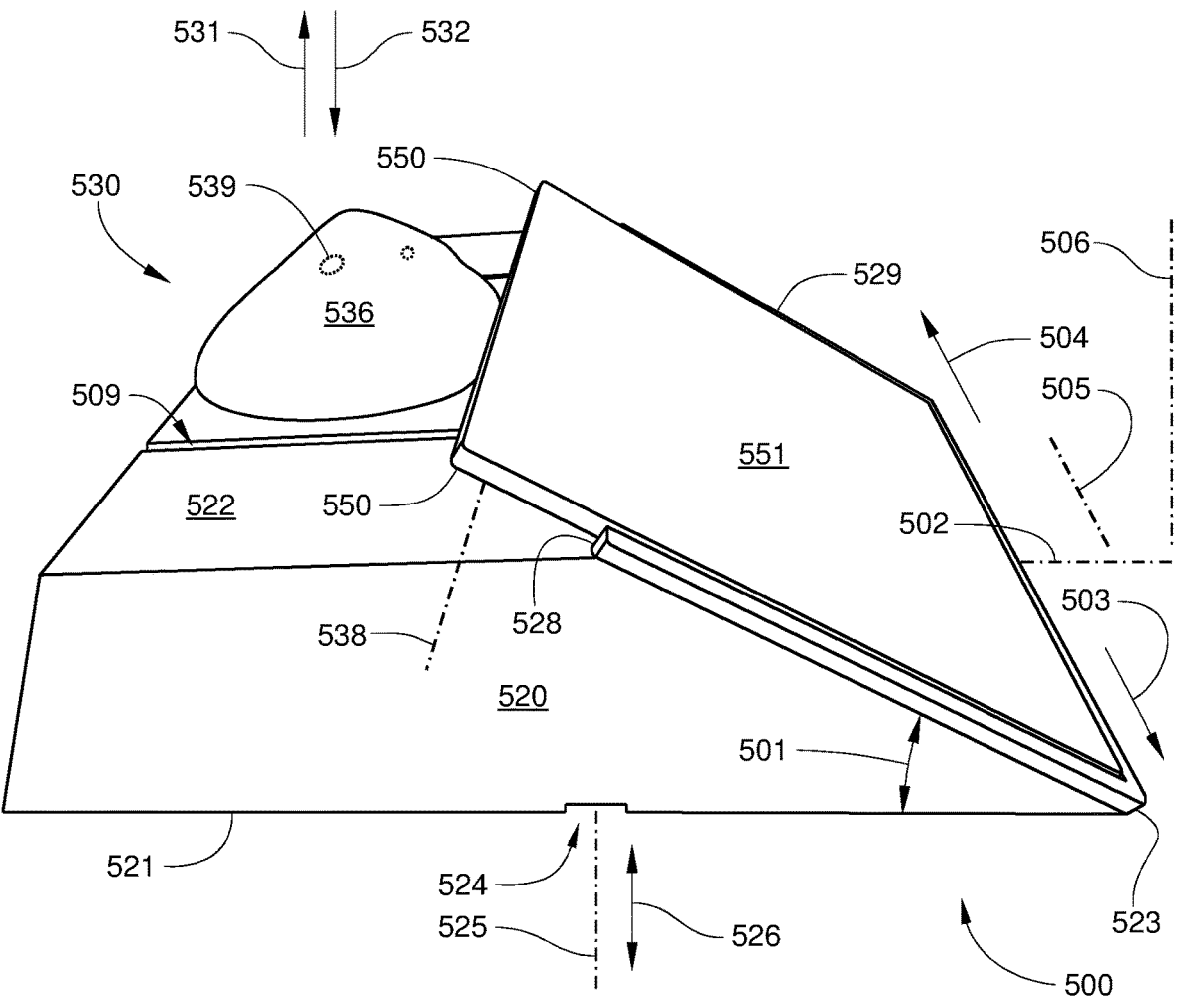
FIG. 5A is a perspective view of a calibration and training apparatus for a treatment delivery system, according to various embodiments.
Figure 5B:
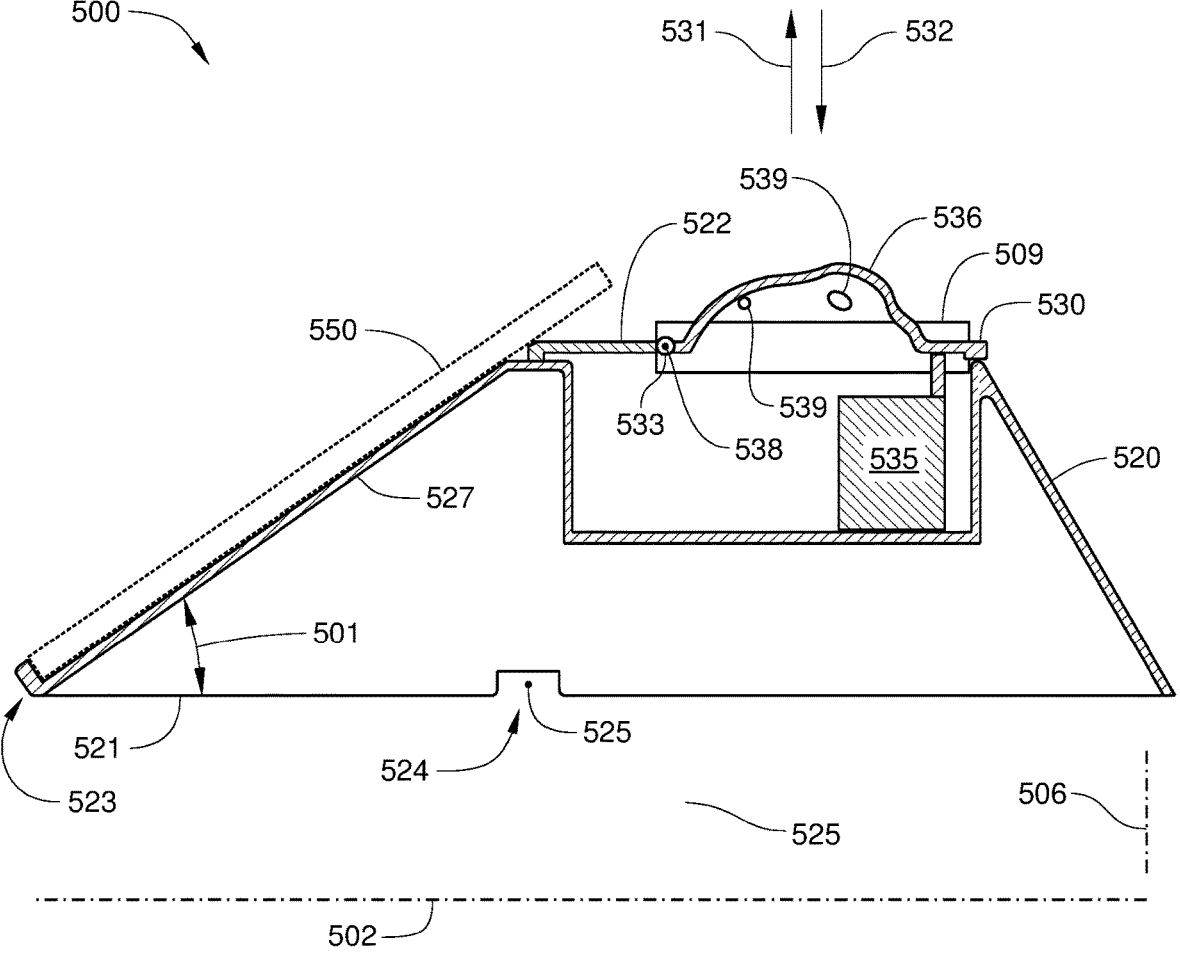
FIG. 5B is a cross-sectional view of the calibration and training apparatus of FIG. 5A, according to various embodiments.

FIG. 5A is a perspective view of a calibration and training apparatus 500 for a treatment delivery system, according to various embodiments. FIG. 5B is a cross-sectional view of calibration and training apparatus 500, according to various embodiments. Calibration and training apparatus 500 supports an optical calibration plate 550 (or other optical calibration device) and positions optical calibration plate 550 at a calibration angle 501. In some embodiments, calibration angle 501 can be an angle of a support surface 527 (shown in FIG. 5B) of optical calibration plate 550 relative to a camera associated with the surface guidance system and/or treatment delivery system, such as patient-monitoring sensors 109 shown in FIG. 1.

Calibration and training apparatus 500 facilitates the accurate positioning of optical calibration plate 550 on a treatment couch (not shown) of the treatment delivery system. Specifically, when calibration and training apparatus 500 is disposed on a treatment couch of the treatment delivery system and supports optical calibration plate 550, calibration and training apparatus 500 enables optical calibration plate 550 to be positioned within a field of view of one or more patient-monitoring sensors of the treatment delivery system, such as field of view 104 of patient-monitoring sensors 109 shown in FIG. 1. In some embodiments, when calibration and training apparatus 500 is disposed on a treatment couch of the treatment delivery system, calibration and training apparatus 500 fixes or otherwise locates optical calibration plate 550 at a calibration position along a longitudinal axis 502 of the treatment couch. In the embodiment illustrated in FIGS. 5A and 5B, calibration and training apparatus 500 includes a base 520 with a movable surface 530.

Base 520 is configured to be positioned on a treatment couch and to support optical calibration plate 550 or another optical calibration device at calibration angle 501. In some embodiments, base 520 includes a material that is partially or completely radiologically transparent and is suitable for use in an environment in which exposure to ionizing radiation occurs. For example, in such embodiments, the material does not cause significant X-ray scattering and does not degrade, discolor, and/or deform when exposed to ionizing radiation. In such embodiments, the material can be a polymer-based material that has sufficient rigidity to support optical calibration plate 550 without deflecting significantly. Additionally or alternatively, in such embodiments, the material can be a material that facilitates one or more manufacturing processes. For example, in embodiments in which some or all of base 520 is printed via a three-dimensional printing process, the material of base 520 can be acrylonitrile butadiene styrene (ABS). In embodiments in which base 520 is formed via an injection molding process, the material of base 520 can be a thermoplastic that has sufficient rigidity and is suitable for frequent exposure to ionizing radiation. Base 520 includes a bottom surface 521, a top surface 522 that opposes bottom surface 521, and a support structure 523. In some embodiments, base 520 includes a material that is not radiologically transparent, such as in instances in which calibration and training apparatus 500 is not employed for the training associated with auto-beam hold functionality of a treatment delivery system. In such embodiments, base 520 and/or other components of calibration and training apparatus 500 can be manufactured from sheet metal or other radiologically opaque materials.

In some embodiments, external surfaces of base 520 and/or other components of calibration and training apparatus 500 can be formed or provided with a matte finish. In such embodiments, reflections from such external surfaces are reduced or minimized.

Bottom surface 521 is configured to enable base 520 to rest stably on a treatment couch surface. Thus, in some embodiments, when a treatment couch has a flat support surface, bottom surface 521 includes a matching flat surface. In addition, bottom surface 521 includes a first indexing feature 524 that is configured to fix or position base 520 at a calibration position along longitudinal axis 502 of the treatment couch by mating with a second indexing feature (not shown). In the embodiment illustrated in FIGS. 5A and 5B, first indexing feature 524 is implemented as a groove or channel that has a major axis 525 that extends in a direction perpendicular to longitudinal axis 502. Thus, in such embodiments, first indexing feature 524 extends laterally. As a result, when first indexing feature 524 mates with the second indexing feature, base 520 can be repositioned in the direction perpendicular to longitudinal axis 502, for example from a first location to a second location. One such embodiment is described below in conjunction with FIG. 6.

Figure 6:
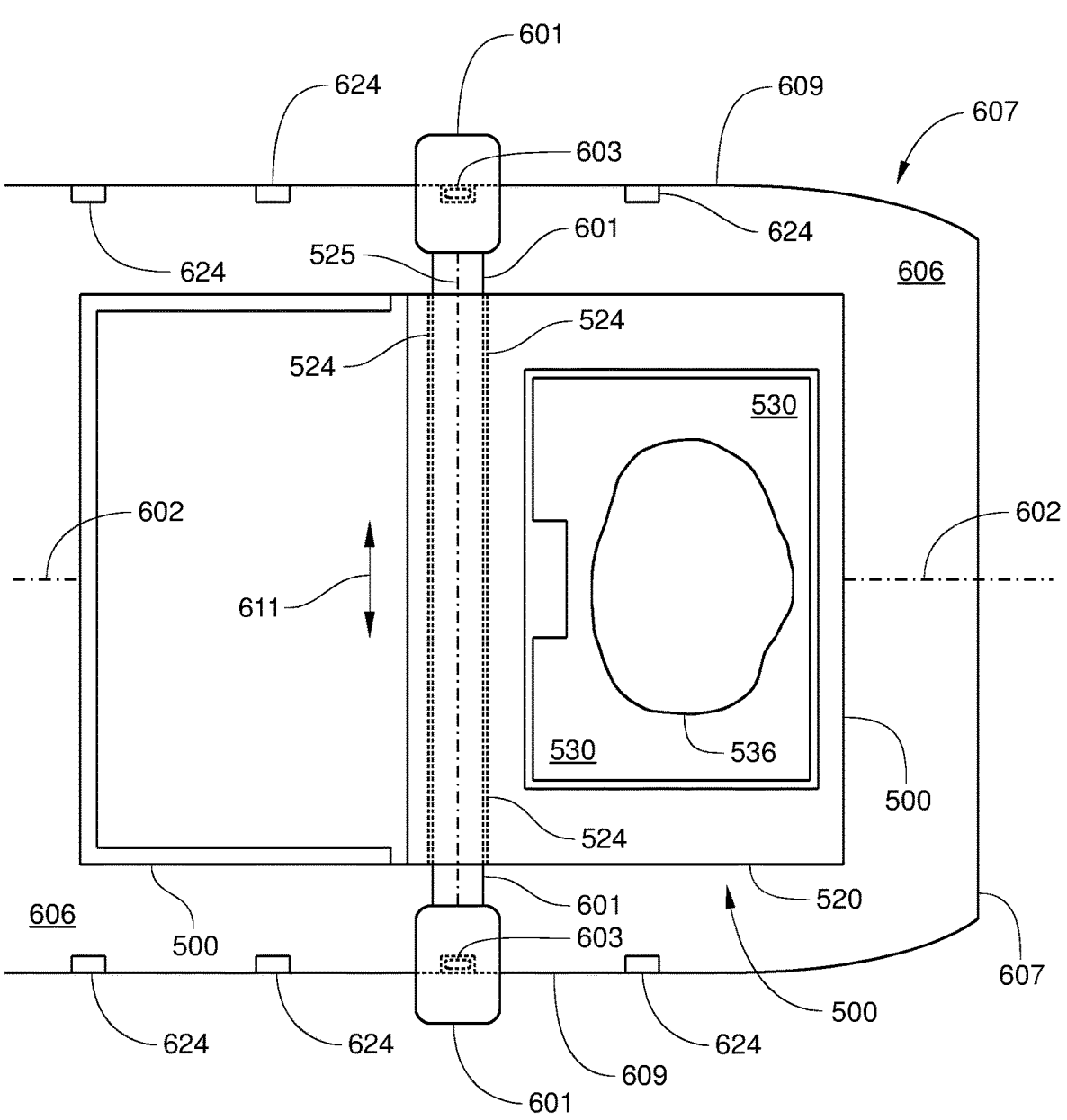
FIG. 6 is a plan view of a calibration and training apparatus disposed on a treatment couch for a treatment delivery system, according to various embodiments.

FIG. 6 is a plan view of calibration and training apparatus 500 disposed on a treatment couch 607 for a treatment delivery system, according to various embodiments. As shown, treatment couch 607 includes one or more pairs of indexing features 624, with one indexing feature 624 of each pair disposed on an opposite side of treatment couch 607. In the embodiment illustrated in FIG. 6, a positioning bar 601 is mounted on treatment couch 607 via one or more pairs of indexing features 624. Each indexing feature 624 can be a feature that is formed in or coupled to a surface of treatment couch 607, such as a top surface 606 (as shown in FIG. 6), a side edge 609, or a bottom surface (not visible in FIG. 6). In some embodiments, each indexing feature 624 includes a concave feature, such as a hole, dimple, depression, or slot. In such embodiments, positioning bar 601 includes one or more complementary protrusions 603 or other features, such as a rod, bump, fin or other convex feature, where each complementary protrusion 603 mates with a corresponding concave feature included in one or more of indexing features 624. Alternatively, in some embodiments, each indexing feature 624 includes a convex feature (such as a rod, bump, fin, or other protrusion), and positioning bar 601 includes one or more complementary convex features (such as a hole, dimple, depression, or slot) that each mate with such protrusions.

In the embodiment illustrated in FIG. 6, a portion of positioning bar 601 acts as a second indexing feature to which first indexing feature 524 of calibration and training apparatus 500 mates. Thus, in such embodiments, the second indexing feature to which first indexing feature 524 mates is included in a device (e.g., positioning bar 601) that can be coupled to one or more third indexing features (e.g., indexing features 624) formed on treatment couch 607. In FIG. 6, first indexing feature 524 is implemented as a slot or groove on a bottom surface of calibration and training apparatus 500, and therefore is indicated with dashed lines. As shown, major axis 525 of first indexing feature 524 extends in a direction 611 that is perpendicular to a longitudinal axis 602 of treatment couch 607. In such embodiments, calibration and training apparatus 500 can be repositioned laterally (i.e., in direction 611) while mated to positioning bar 601, so that calibration and training apparatus 500 remains fixed in the same position along longitudinal axis 602 of treatment couch 607. Thus, in such embodiments, calibration and training apparatus 500 can be repositioned laterally while calibration and training apparatus 500 remains fixed at a longitudinal position and an optical calibration device (not shown) supported by calibration and training apparatus 500 remains oriented at a desired calibration angle.

Alternatively, in some embodiments, first indexing feature 524 of calibration and training apparatus 500 is configured to mate with one or more complementary indexing features 624 that are formed on a surface of treatment couch 607. Thus, in such embodiments, the second indexing feature to which first indexing feature 524 mates is included in treatment couch 607. For example, in one such embodiment, first indexing feature 524 includes a pair of protrusions for mating with a pair of indexing features 624. In another example embodiment, indexing features 624 are configured as lateral grooves (not shown) formed in treatment couch 607 instead of pairs of convex features, and first indexing feature 524 includes a lateral fin or ridge that mates with a particular lateral groove formed in treatment couch 607. In such embodiments, calibration and training apparatus 500 can be repositioned laterally while calibration and training apparatus 500 remains fixed at a longitudinal position and an optical calibration device (not shown) supported by calibration and training apparatus 500 remains oriented at a calibration angle.

In other examples embodiments, any other combination of complementary features can be employed for first indexing feature 524 and indexing features 624.

Returning to FIGS. 5A and 5B, support structure 523 forms at least a portion of a side of base 520. Support structure 523 positions a calibration surface 551 of optical calibration device 550 at calibration angle 501 when base 520 is disposed on a patient-receiving surface of the treatment couch. Typically, calibration surface 551 includes various precisely arranged markings that facilitate calibration of a surface guidance system, such as circles, rectangles, and the like. It is noted that, when first indexing feature 524 is mated with a corresponding second indexing feature (such as a portion of positioning bar 601 or one or more indexing features 624 in FIG. 6), optical calibration device 550 remains at calibration angle 501 when base 520 is repositioned laterally from a first location to a second location (e.g., along a direction 526 perpendicular to longitudinal axis 502). In the embodiment illustrated in FIGS. 5A and 5B, support structure 523 includes support surface 527, a first stop 528, and a second stop 529.

Support surface 527 supports optical calibration device 550 when calibration and training apparatus 500 is disposed on a patient-receiving surface of a treatment couch. As shown, support surface 527 is oriented at calibration angle 501 when calibration and training apparatus 500 is disposed on a patient-receiving surface of a treatment couch. Consequently, when optical calibration device 550 is disposed on support surface 527, optical calibration device 550 is also oriented at calibration angle 501.

First stop 528 and a second stop 529 prevent motion of optical calibration device 550, when resting on support surface 527, in a direction perpendicular to longitudinal axis 502 of the treatment couch. For example, in the embodiment illustrated in FIGS. 5A and 5B, first stop 528 prevents motion of optical calibration device 550 in a first direction 503 and second stop 529 prevents motion of optical calibration device 550 in a second direction 504. In some embodiments, first stop 528 and second stop 529 are configured to center the positioning of optical calibration device 550 on support surface 527.

Movable surface 530 enables the clinical simulation of patient motion associated with the respiratory cycle without the use of a trainer or patient lying on a treatment couch of a treatment delivery system. Movable surface 530 is included in a surface of calibration and training apparatus 500 that is within a field of view of one or more patient-monitoring sensors of the treatment delivery system, such as field of view 104 of patient-monitoring sensors 109 shown in FIG. 1. For example, in some embodiments, movable surface 530 is included in top surface 522 of base 520. In some embodiments, movable surface 530 can be actuated in a first direction 531 away from a treatment couch that supports calibration and training apparatus 500 and in a second direction 532 toward the treatment couch. For example, in some embodiments, calibration and training apparatus 500 includes an actuator 535 that generates such motion. In the embodiment illustrated in FIGS. 5A and 5B, actuator 535 is coupled to movable surface 530 and causes movable surface 530 to hinge upward (e.g., in first direction 531) and downward (e.g., in second direction 532) about a rotatable coupling 533 (shown in FIG. 5B). Generally, actuator 535 can be any technically feasible actuator that can be coupled to movable surface 530 and cause movable surface 530 to selectively move in first direction 531 and second direction 532. In some embodiments, actuator 535 includes an electric motor, a pneumatically actuated piston, a stepper motor, and/or the like. In one embodiment, actuator 535 includes a Breathing Gating Assembly (P-10003157703) available from Varian, Inc., Palo Alto, Calif.

In the embodiment illustrated in FIGS. 5A and 5B, movable surface 530 is rotatably coupled to top surface 522 of base 520 via a hinge or other rotatable coupling 533. Thus, in such an embodiment, rotation of movable surface

530 about rotatable coupling 533 causes movable surface 530 to selectively move in first direction 531 and second direction 532. For example, in one such embodiment, rotatable coupling 533 enables rotation of movable surface 530 about an axis of rotation 538 that is perpendicular to longitudinal axis 502. In such embodiments, axis of rotation 538 can be disposed in a plane that is parallel to the patient-receiving surface of the treatment couch. In other embodiments, movable surface 530 is not rotatably coupled to top surface 522. In such embodiments, at least a portion of movable surface 530 is caused to selectively move in first direction 531 and second direction 532 by actuator 535 without rotation about an axis of rotation. In either case, motion of movable surface 530 enables the clinical simulation of patient motion associated with the respiratory cycle without the use of a trainer or patient lying on a treatment couch of a treatment delivery system.

In some embodiments, movable surface 530 includes an anthropomorphic surface 536 that can more accurately simulate a surface of a patient chest wall during a respiratory cycle. In such embodiments, anthropomorphic surface 536 is asymmetrical about one or more axes. For example, in some embodiments, anthropomorphic surface 536 is asymmetrical about one or two axes that are parallel to a top surface of the treatment couch, such as longitudinal axis 502 and/or a lateral axis 505 of the treatment couch. Additionally or alternatively, in some embodiments, anthropomorphic surface 536 is asymmetrical about an axis that is perpendicular to a top surface of the treatment couch, such as vertical axis 506 of the treatment couch. Such asymmetries facilitate more realistic simulations of chest wall motion during a respiratory cycle.

In some embodiments, movable surface 530 includes one or more radiologically opaque markers 539 (also referred to as fiducial markers) that are coupled to movable surface 530. In such embodiments, an auto-beam hold functionality of a treatment delivery system can be simulated, in which X-ray imaging monitors implanted fiducials in a patient during radiation treatment. Thus, calibration and training apparatus 500 enables the training for and/or demonstration of auto-beam hold without patient involvement. In some embodiments, radiologically opaque markers 539 include a material that is readily visible in X-ray images, such as a metal-containing material or other radiologically dense material. In some embodiments, radiologically opaque markers 539 are regular in shape and/or identical to each other in shape. Alternatively or additionally, in some embodiments, radiologically opaque markers 539 are irregular in shape. Alternatively or additionally, in some embodiments, one or more of radiologically opaque markers 539 have different shapes. Thus, in such embodiments, a first radiologically opaque marker 539 has a first shape and a second radiologically opaque marker 539 has a second shape that is different than the first shape.

In the embodiment illustrated in FIGS. 5A and 5B, radiologically opaque markers 539 are shown coupled to and/or disposed on movable surface 530. In other embodiments, one or more of radiologically opaque markers 539 can be embedded in anthropomorphic surface 536. Alternatively or additionally, in some embodiments, one or more channels are formed in anthropomorphic surface 536, where each channel can accommodate a radiologically opaque markers 539 for training and/or demonstration purposes. In such embodiments, anthropomorphic surface 536 can be readily modified with one or more different radiologically opaque markers 539.

In some embodiments, calibration and training apparatus 500 includes one or more surfaces 509 or rails that prevent movable surface 530 from moving in a direction perpendicular to first direction 531 or second direction 532. For example, in the embodiment illustrated in FIGS. 5A and 5B, surfaces 509 are disposed proximate edges of movable surface 530. In addition, surfaces 509 are planar surfaces that are oriented parallel to first direction 531 and second direction 532. Thus, when movable surface 530 rotates about axis of rotation 538, surfaces 509 can act as rails that prevent or reduce motion of movable surface 530 in a direction perpendicular to first direction 531 and second direction 532.

Calibration and Training Procedures

According to various embodiments, calibration and training apparatus 500 is employed during calibration and/or training procedures associated with a surface guidance system of a treatment delivery system, such as treatment delivery system 100. In such embodiments, calibration and training apparatus 500 supports an optical calibration plate 550 (or other optical calibration device) and positions optical calibration plate 550 at a calibration angle 501. In addition, calibration and training apparatus 500 facilitates the accurate positioning and repositioning of optical calibration plate 550 on a treatment couch the treatment delivery system during a calibration procedure. One such embodiment is described below in conjunction with FIG. 7.

Figure 7:
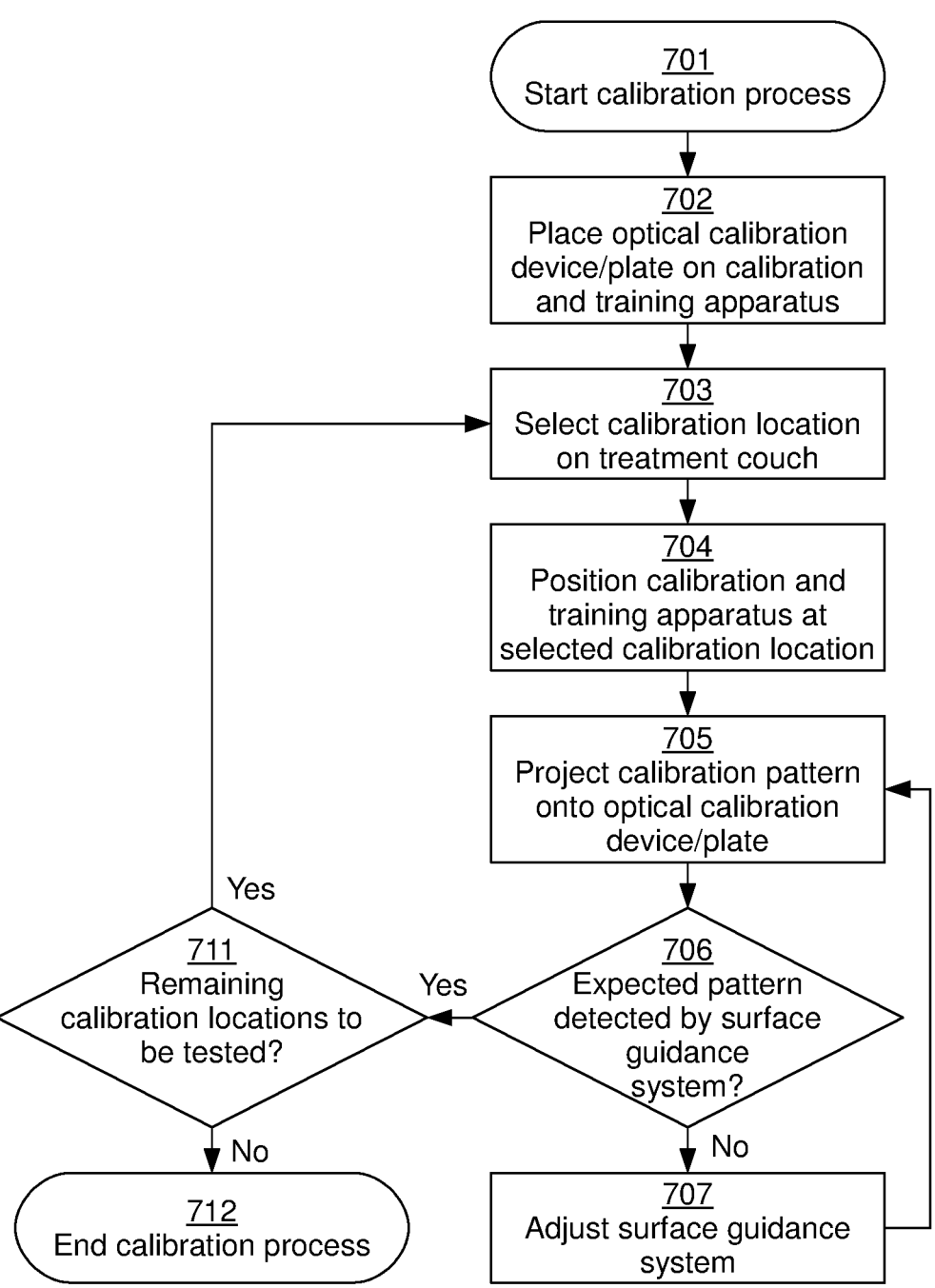
FIG. 7 set forth a flowchart of a calibration process for a surface guidance system associated with a treatment delivery system, according to one or more embodiments.

FIG. 7 set forth a flowchart of a calibration process 700 for a surface guidance system associated with a treatment delivery system, according to one or more embodiments. In some embodiments, calibration process 700 can be performed as part of the initial commissioning of a particular treatment delivery system. Alternatively or additionally, in some embodiments, calibration process 700 can be performed periodically and/or in response to certain triggering events, such as errors associated with the surface guidance system during operation.

Calibration process 700 may include one or more operations, functions, or actions as illustrated by one or more of blocks 701-712. Although the blocks are illustrated in a sequential order, these blocks may be performed in parallel, and/or in a different order than those described herein. Also, the various blocks may be combined into fewer blocks, divided into additional blocks, and/or eliminated based on the desired implementation. Although method 700 is described in conjunction with treatment delivery system 100 and FIGS. 1, 2, 3, 4, 5A, 5B, and 6, persons skilled in the art will understand that the performance of calibration process 700 by any suitably configured treatment delivery system is within the scope of the present embodiments.

In step 701, calibration process 700 is started. As noted above, calibration process 700 can be performed as part of the initial commissioning of a particular treatment delivery system, periodically, and/or in response to certain triggering events.

In step 702, optical calibration device 550 is placed on calibration and training apparatus 500. For example, in some embodiments, optical calibration device 550 is placed on support surface 527 of calibration and training apparatus 500 so that calibration surface 551 is oriented at calibration angle 501 relative to a patient-receiving surface of couch 107.

In step 703, a user selects a particular location on couch 107 within field of view 104 of one or more patient-monitoring sensors 109. In some embodiments, the particular location selected includes a specified longitudinal position on couch 107. In addition, in some embodiments, the particular location selected includes a specified lateral position on couch 107, such as a particular position along lateral axis 505 of couch 107.

In step 704, the user positions calibration and training apparatus 500 at the calibration position selected in step 703. In some embodiments, calibration and training apparatus 500 is positioned at the selected calibration position by mating first indexing feature 524 with a second indexing feature, such as a positioning bar 601 that is mounted on couch 107 or one or more pairs of indexing features 624 formed on or coupled to couch 107. In some embodiments, after the initial placement of calibration and training apparatus 500, in step 704 the user positions calibration and training apparatus 500 at the selected calibration position by moving calibration and training apparatus 500 laterally on couch 107. Thus, optical calibration device 550 remains oriented at calibration angle 501. It is noted that in such embodiments, calibration and training apparatus 500 can be slid laterally along positioning bar 601.

In step 705, the surface guidance system projects a specified calibration pattern onto optical calibration device 550, for example via projector 201 and/or calibration LED 203. In some embodiments, the specific calibration pattern includes a speckle pattern.

In step 706, a user performing calibration process 700 and/or a controller of the surface guidance determines whether an expected pattern is detected by the surface guidance system. If yes, calibration process 700 proceeds to step 707; if no, calibration process 700 proceeds to step 711.

In step 707, a user performing calibration process 700 adjusts the surface guidance system. For example, in some embodiments, locations and/or orientations of one or more patient-monitoring sensors 109 are adjusted. Calibration process 700 then returns to step 705 for another iteration of calibration pattern projection.

In step 711, a user performing calibration process 700 and/or a controller of the surface guidance determines whether there are any remaining locations to be tested? If yes, calibration process 700 returns to step 703; if no, calibration process 700 proceeds to step 712 and terminates.

Use of calibration and training apparatus 500 in the performance of calibration process 700 enables the repositioning of optical calibration device 550 to be performed without affecting the orientation of optical calibration device 550 relative to one or more patient-monitoring sensors 109 of the surface guidance system. In addition, such use of calibration and training apparatus 500 enables the accurate positioning of optical calibration device 550 along longitudinal axis 502 of couch 107. As a result, alignment of an isocenter of a surface guidance system to an isocenter of treatment delivery system 100, such as isocenter 303 or isocenter 403, can be performed much more quickly than via conventional calibration methods and with significantly less error.

According to various embodiments, calibration and training apparatus 500 is employed during demonstration and/or training procedures associated with a surface guidance system of a treatment delivery system, such as treatment delivery system 100. In such embodiments, calibration and training apparatus 500 enables the demonstration of one or more use cases of a surface guidance system of treatment delivery system 100. For example, in some instances, a user, such as a trainer or demonstrator, positions calibration and training apparatus 500 at a suitable training position for a particular use case of treatment delivery system 100. In some embodiments, calibration and training apparatus 500 is positioned at the suitable training position by mating first indexing feature 524 with a second indexing feature, such as a positioning bar 601 that is mounted on couch 107 or one or more pairs of indexing features 624 formed on or coupled to couch 107. In some embodiments, actuator 535 is activated at this time, and movable surface 530 begins motion simulating chest wall motion that occurs during the respiratory cycle. After calibration and training apparatus 500 is positioned on couch 107 and actuator 535 is activated, training that is associated with one or more use cases of treatment delivery system 100 and relies on chest wall motion can then performed. For example, in some instances, the auto-beam hold functionality of treatment delivery system 100 can be demonstrated and/or clinical users of treatment delivery system 100 trained on such functionality without a patient being involved. Alternatively or additionally, in some instances, radiation treatment with respiratory gating can be demonstrated and/or clinical users of treatment delivery system 100 trained on such functionality without a patient being involved.

Throughout the present disclosure, the terms "first," "second," "third," etc. do not denote any order of importance, but are rather used to distinguish one element from another. Independent of the grammatical term usage, individuals with male, female or other gender identities are included within the term.

While various aspects and embodiments have been disclosed herein, many modifications and variations will be apparent to those of ordinary skill in the art without departing from the scope and spirit of the described embodiments. The various aspects and embodiments disclosed herein are for purposes of illustration and are not intended to be limiting, with the true scope and spirit being indicated by the following claims.

The invention claimed is:

1. An apparatus for a treatment delivery system, the apparatus comprising:
   a base for resting on a couch of the treatment delivery system;
   a support structure for positioning a surface of an optical calibration device at a calibration angle; and
   a first indexing feature that is formed on a bottom surface of the base and is configured to fix the base at a calibration position along a longitudinal axis of the couch by mating with a second indexing feature.

2. The apparatus of claim 1, wherein the second indexing feature is formed on the couch of the treatment delivery system.

3. The apparatus of claim 1, wherein the second indexing feature is included in a device that can be coupled to one or more third indexing features formed on the couch of the treatment delivery system.

4. The apparatus of claim 3, wherein the one or more third indexing features comprise a pair of positioning features formed on the couch.

5. The apparatus of claim 1, wherein a major axis of the first indexing feature extends in a direction perpendicular to the longitudinal axis.

6. The apparatus of claim 5, wherein, when the first indexing feature mates with the second indexing feature, the base can be repositioned in the direction perpendicular to the longitudinal axis from a first location to a second location.

7. The apparatus of claim 6, wherein the support structure positions the surface of the optical calibration device at the calibration angle when the base is disposed at the first location or at the second location.

8. The apparatus of claim 5, wherein the first indexing feature extends from a first side of the base to a second side of the base that opposes the first side.

9. The apparatus of claim 1, wherein the support structure includes a support surface that is oriented at the calibration angle when the apparatus is disposed on the couch of the treatment delivery system.

10. The apparatus of claim 1, wherein the support structure includes:
   a first stop that prevents motion of the optical calibration device, when resting on the support surface, in a first direction perpendicular to the longitudinal axis of the couch; and
   a second stop that prevents motion of the optical calibration device, when resting on the support surface, in a second direction perpendicular to the longitudinal axis of the couch, wherein the second direction is opposite the first direction.

11. The apparatus of claim 1, further comprising a movable surface that can visually simulate chest wall motion during a respiratory cycle.

12. The apparatus of claim 11, wherein the support structure forms at least a portion of a first side of the base and the movable surface forms at least a portion of a second side of the base.

13. The apparatus of claim 1, wherein, when the optical calibration device is disposed on the support structure and the first indexing feature mates with the second indexing feature, the surface of an optical calibration device is within a field of view of a camera associated with the treatment delivery system.

14. The apparatus of claim 1, wherein the calibration angle comprises an angle of a surface of the calibration relative to a patient-receiving surface of the couch.

* * * * *